United States Patent
Ferrari et al.

(10) Patent No.: US 8,962,904 B2
(45) Date of Patent: Feb. 24, 2015

(54) CATALYTIC COMPOSITION FOR PRODUCTION OF ALPHA-OLEFINS

(75) Inventors: Daniela Ferrari, Antwerp (BE); Alberto Martinez Joaristi, Antwerpen (BE); Billy B. Bardin, Lake Jackson, TX (US); Garmt R. Meima, Terneuzen (NL)

(73) Assignee: Dow Global Technologies LLC, Midland, MI (US)

( * ) Notice: Subject to any disclaimer, the term of this patent is extended or adjusted under 35 U.S.C. 154(b) by 29 days.

(21) Appl. No.: 13/519,899

(22) PCT Filed: Dec. 14, 2010

(86) PCT No.: PCT/US2010/003159
§ 371 (c)(1),
(2), (4) Date: Jun. 29, 2012

(87) PCT Pub. No.: WO2011/090463
PCT Pub. Date: Jul. 28, 2011

(65) Prior Publication Data
US 2012/0277513 A1 Nov. 1, 2012

Related U.S. Application Data

(60) Provisional application No. 61/290,779, filed on Dec. 29, 2009.

(51) Int. Cl.
| | | |
|---|---|---|
| C07C 1/20 | (2006.01) |
| C07C 1/24 | (2006.01) |
| C07C 1/00 | (2006.01) |
| B01J 23/843 | (2006.01) |
| B01J 23/78 | (2006.01) |
| B01J 23/80 | (2006.01) |
| B01J 23/825 | (2006.01) |
| B01J 23/835 | (2006.01) |
| B01J 37/02 | (2006.01) |

(52) U.S. Cl.
CPC .............. B01J 23/8437 (2013.01); B01J 23/78 (2013.01); B01J 23/80 (2013.01); B01J 23/825 (2013.01); B01J 23/835 (2013.01); B01J 37/0201 (2013.01); C07C 1/20 (2013.01); C07C 2521/10 (2013.01); C07C 2523/14 (2013.01); C07C 2523/72 (2013.01); C07C 2523/78 (2013.01); C07C 2523/80 (2013.01); C07C 2523/825 (2013.01)
USPC ............................ 585/639; 585/638; 585/640

(58) Field of Classification Search
USPC ........................................................ 585/639
See application file for complete search history.

(56) References Cited

U.S. PATENT DOCUMENTS

| | | | |
|---|---|---|---|
| 4,234,752 A | 11/1980 | Wu et al. | |
| 4,895,816 A * | 1/1990 | Gardner et al. | ................. 502/10 |
| 5,030,792 A | 7/1991 | Slaugh | |
| 7,030,286 B2 | 4/2006 | Röttger et al. | |
| 7,342,144 B2 * | 3/2008 | Kaizik et al. | ................. 585/640 |
| 7,368,621 B2 | 5/2008 | Krissmann et al. | |
| 2003/0065233 A1 | 4/2003 | Fuji et al. | |
| 2003/0220192 A1 | 11/2003 | Tanev | |
| 2007/0100186 A1 | 5/2007 | Gao et al. | |
| 2007/0203381 A1 | 8/2007 | Gao et al. | |

FOREIGN PATENT DOCUMENTS

| | | |
|---|---|---|
| CN | 1158277 | 9/1997 |
| CN | 1165053 | 11/1997 |
| EP | 0183861 | 6/1986 |
| EP | 1205235 | 5/2002 |
| EP | 2186784 | 5/2010 |
| GB | 1499199 | 1/1978 |
| GB | 1499297 | 1/1978 |
| WO | 9210450 | 6/1992 |
| WO | 03024910 | 3/2003 |
| WO | 2005019139 | 3/2005 |

OTHER PUBLICATIONS

International Search Report and Written Opinion from related PCT application PCT/US2010/003159 dated May 3, 2011, 17 pages.
International Preliminary Report on Patentability from related PCT application PCT/US2010/003159 dated Dec. 9, 2011, 16 pages.
Wang, et al. "Producing of 1-octene from Methyl Octyl Ether by Telomeric Reaction of Butadiene", Petrochemical Technology, Issue 3, vol. 32, 2003, 200-204.

* cited by examiner

*Primary Examiner* — Bobby Ramdhanie
*Assistant Examiner* — Youngsul Jeong
(74) *Attorney, Agent, or Firm* — Brooks, Cameron & Huebsch, PLLC

(57) ABSTRACT

Catalytic composition for producing an alpha-olefin and methods of making same. The catalytic composition includes a gamma-alumina substrate dopes with at least one element consisting of bismuth, copper, gallium, phosphorus, tin, and zinc, an amount of each element being within a range of from 150 parts per million to 1000 parts per million relative to a total doped weight of the gamma-alumina substrate. Additionally, at least one element is combined with at least one element consisting of cesium, lithium, and magnesium, an amount of each element being within the range of from 150 parts per million to 1000 parts per million relative to the total doped weight of the gamma-alumina substrate.

5 Claims, No Drawings

CATALYTIC COMPOSITION FOR PRODUCTION OF ALPHA-OLEFINS

This application is a National Stage application under 35 U.S.C. 371 of PCT/US2010/003159, filed on Dec. 14, 2010 and published as WO2011/090463 A1 on Jul. 28, 2011, which claims the benefit of U.S. Provisional Application Ser. No. 61/290,779 filed Dec. 29, 2009, the entire contents of which are incorporated herein by reference in its entirety.

The present disclosure relates to a number of catalytic compositions for production of alpha-olefins (α-olefins), and in particular for improving production of the 1-octene by catalytically cleaving a methyl-octyl ether (MOE) precursor with a doped catalyst substrate and increasing a MOE precursor conversion and/or a selectivity, purity, and/or yield of a particular α-olefin under some conditions relative to an undoped substrate.

Among other commercial uses, α-olefins are used as co-monomers for polymerization into plastics, e.g., polyethylene. Such α-olefins require a minimum level of purity for polymerization into a plastic having desired characteristics. 1-octene is one example of an α-olefin used for polymerization into a linear low density polyethylene (LLDPE). 1-octene purity is defined as the ratio between 1-octene and its isomers. MOE conversion is defined as the molar fraction of the MOE precursor that is converted during a reaction. Generally, the purity of 1-octene decreases with increasing conversion of the MOE precursor into 1-octene and undesired isomers of octene increase. The undesired isomers of octene contain a carbon double bond in a position other than the 1-position.

Various catalysts are used for production of α-olefins from a precursor with a methyl group having an ether linkage to a straight chain alkane with at least four carbon atoms. For example, an undoped γ-alumina substrate is used for conversion of a MOE precursor to yield 1-octene. At a temp. of 290° C., an undoped γ-alumina substrate initially achieves a desired purity, e.g., at least 96.0, and selectivity, e.g., at least 90.0, of 1-octene as measured on a molar percentage (mol %) basis. However, the 1-octene purity and selectivity both decrease with increasing conversion of the MOE precursor into 1-octene when using the undoped γ-alumina substrate at 290° C. and above.

At a lower temp., e.g., 260° C., both the conversion of the MOE precursor with the undoped γ-alumina substrate and the selectivity to 1-octene are notably reduced compared to a level obtained in initial conversions with the undoped γ-alumina substrate at 290° C. Maintaining a mol % conversion level of the MOE precursor ([MOE]$_{conv}$) that is acceptable, e.g., at least 75.0, is achievable at a temp. lower than 290° C. with a doped catalyst substrate while also increasing a mol % of 1-octene selectivity ([1-octene]$_{sel}$), as shown in the table below.

The present disclosure describes a catalytic composition for producing a number of α-olefins formed by doping of a γ-alumina substrate with at least one element selected from a group consisting of bismuth (Bi), copper (Cu), gallium (Ga), phosphorus (P), tin (Sn), and zinc (Zn). An amount of each element used in the doping is within a range of from 150 parts per million (ppm) to 1,000 ppm relative to a total doped weight of the γ-alumina substrate. The doped catalytic composition has an improved ability to produce α-olefins relative to an undoped γ-alumina substrate. The doped catalytic compositions catalytically cleave the MOE precursor. The yield of 1-octene in mol % ([1-octene]$_{yld}$) is increased by improving the selectivity to 1-octene and/or the conversion of the MOE precursor at the desired mol % of 1-octene purity ([1-octene]$_{pur}$) relative to the undoped γ-alumina substrate, as shown in the table below.

The present disclosure also describes a catalytic composition formed by doping of the γ-alumina substrate with at least one element selected from the group consisting of Bi, Cu, Ga, P, Sn, and Zn, of which at least one element is combined when doping with at least one element consisting of cesium (Cs), lithium (Li), and magnesium (Mg). An amount of each of these elements is within a range of from 150 ppm to 1,000 ppm relative to the total doped weight of the γ-alumina substrate.

U.S. Pat. No. 7,342,144, assigned to OXENO Olefinchemie GmbH, shows catalysts for producing α-olefins from a MOE precursor that include alkali metals, e.g., Cs and Li, and alkaline earth metals, e.g., Mg. However, the reference shows these metals being used individually or in combination with each other. The reference does not describe a catalytic composition formed with at least one element selected from the group consisting of Bi, Cu, Ga, P, Sn, and Zn, in particular where the at least one element is combined with at least one element consisting of Cs, Li, and Mg.

Formulas for calculation of conversion, selectivity, yield, and other productivity parameters are shown below with all amounts being in moles:

$$[MOE]_{conv} = \frac{\text{input of } MOE\,[MOE]_{in} - \text{output of } MOE([MOE]_{out})}{[MOE]_{in}} \times 100$$

$$[1\text{-octene}]_{sel} = \frac{\text{output of [1-octene]}}{\text{output of [total product]}} \times 100$$

$$[1\text{-octene}]_{pur} = \frac{\text{output of [1-octene]}}{\text{output of ([1-octene]} + \text{[octene isomers])}} \times 100$$

$$[1\text{-octene}]_{yld} = [MOE]_{conv} \times [1\text{-octene}]_{sel} / 100$$

Dopant elements in the group described are used either individually or combined in the doping. The doped catalytic compositions are generally prepared for testing as follows, although variations in preparation, concentration and/or impregnation, among other parameters, are within the scope of this disclosure.

Suitable Bi, Cs, Cu, Ga, Li, Mg, P, Sn, and Zn dopant element precursors are obtained from vendors that market compounds containing these elements. Compounds containing the dopant elements are listed respectively as follows along with a corresponding CAS number: bismuth nitrate pentahydrate 10035-06-0; cesium nitrate 7789-18-6; copper (II) nitrate hemipentahydrate 19004-19-4; gallium (III) nitrate hydrate 69365-72-6; lithium nitrate 12333-11-8; magnesium nitrate hexahydrate 134477-34-4; ammonium hydrogen phosphate 7783-28-0; tin (II) chloride 7772-99-8; and zinc nitrate hexahydrate 1310-58-3. These dopant element precursors are dissolved to achieve a desired stock concentration in an appropriate solvent to form a stock solution.

A suitable γ-alumina, e.g., CAS number 11092-32-3 or 90669-62-8, is the substrate for the doped catalytic compositions. The γ-alumina is also the reference comparative catalyst (Comp).

As an example of laboratory scale preparation and testing of a catalytic composition, an amount of the γ-alumina substrate, e.g., 250-260 milligrams (mg), is deposited in a vial. Stock solutions of catalytic precursor compounds are prepared and impregnation solutions are prepared by taking desired amounts of the stock solutions of precursor compounds and, when more than one catalytic precursor compound is used, mixing the stock solutions.

During the impregnation process, a vial containing the γ-alumina substrate is shaken and, after drop-wise addition of impregnation solution, the contents of each tube are stirred. The impregnated substrate is then dried under low vacuum at 90° C. for 3 hours (hrs) and transferred into a container for storage.

In order to perform catalytic testing, approximately 200 microliters (μl) of each catalytic composition is loaded into a reactor, as is the γ-alumina substrate. The reactor is a stainless steel tube with an internal diameter of 3.8 millimeters (mm) and a length of 135 mm. The stainless steel tube is placed in a ceramic heating block and electrically heated. The reactor is heated in flowing nitrogen ($N_2$) gas from ambient temp. to 270° C. at atmospheric pressure. The temp. is measured by a thermocouple situated above the catalyst bed. The temp. is controlled by a thermocouple placed in the heating block. The MOE precursor feed is gasified in a preheating zone maintained at the same temp., after which the MOE precursor is fed to the reactor. The MOE precursor is fed to the reactor at a feed rate of 0.4 grams per hour (g/hr) at 270° C. and 8 milliliter/minute (ml/min) of 13% $N_2$ in helium are fed to the reactor at a pressure of 250 kPa. The reaction is allowed to stabilize at 270° C. for 12-15 hr. For testing, the temp. is varied between 275° C. and 290° C. for the doped catalyst compositions and between 260° C. to 290 ° C. for the undoped γ-alumina substrate. The gas product is analyzed by gas chromatography (GC) using thermal conductivity (TC) and flame ionization (FI) detectors.

EXAMPLES (EXS)/COMPARATIVES (COMPS)

| Exs/ Comps | Dopant Elements | Temp. (° C.) | $[MOE]_{conv}$ (mol %) | $[1-octene]_{pur}$ (mol %) | $[1-octene]_{sel}$ (mol %) | $[1-octene]_{yld}$ (mol %) |
|---|---|---|---|---|---|---|
| Comp 1 | None | 290 | 97.9 | 93.6 | 92.7 | 90.7 |
| Comp 2 | None | 260 | 62.8 | 96.8 | 89.9 | 56.4 |
| Ex 1 | Cu 600 | 290 | 86.6 | 96.1 | 92.1 | 79.7 |
| Ex 2 | Cu 600/Zn 400 | 290 | 81.8 | 96.4 | 94.4 | 77.2 |
| Ex 3 | Cu 300/Ga 300 | 275 | 74.1 | 96.2 | 93.9 | 69.5 |
| Ex 4 | Cu 300/Li 300 | 290 | 77.1 | 96.7 | 94.1 | 72.5 |
| Ex 5 | Cu 300/Mg 300 | 290 | 85.4 | 96.3 | 92.0 | 78.6 |
| Ex 6 | Sn 600/Li 400 | 280 | 76.4 | 97.1 | 91.9 | 70.2 |
| Ex 7 | Bi 300/Cs 300 | 275 | 75.2 | 96.1 | 91.0 | 68.4 |
| Ex 8 | P 300/Mg 300 | 275 | 78.3 | 96.2 | 91.7 | 71.8 |

The above table shows the results with either a single catalytic dopant or a combination of 2 dopant elements being used, as denoted by Ex, as contrasted to the undoped γ-alumina substrate, as denoted by Comp. The table shows that the γ-alumina substrate is usually doped with 600 ppm when a single element is used as a dopant and is usually doped with 300 ppm of each of 2 elements when the 2 are combined as dopants. However, varying amounts of each element in the group of Bi, Cs, Cu, Ga, Li, Mg, P, Sn, and Zn are used as dopants, as shown by some of the combinations in the table, and remain within the range of from 150 ppm to 1,000 ppm relative to the total doped weight of the γ-alumina substrate. For instance, in Ex 2 600 ppm Cu is combined with 400 ppm Zn and in Ex 5 600 ppm Sn is combined with 400 ppm Li. The values shown in the table for $[MOE]_{conv}$, $[1-octene]_{pur}$, $[1-octene]_{sel}$, and $[1-octene]_{yld}$ are in mol % calculated using the formulas presented above.

Referring to Ex 2 in the above table to illustrate catalytic composition preparation, impregnate 250 mg of γ-alumina with 197 μl of a solution containing 0.012 moles of copper nitrate hemipentahydrate per liter (mol/l) and 0.008 mol/l of zinc nitrate hexahydrate dissolved in water ($H_2O$). Dry the sample at 90° C. for 2 hrs and then calcine at 450° C. for 3 hrs. The amount of Cu in the total doped weight of the γ-alumina substrate is 600 ppm and the amount of Zn is 400 ppm Ex 1: Replicate Ex 2 but impregnate 500 mg γ-alumina with 404 μl of a solution containing 0.012 mol/l of copper nitrate hemipentahydrate dissolved in $H_2O$. The amount of Cu in the total doped weight of the γ-alumina substrate is 600 ppm.

Ex 3: Replicate Ex 2 but impregnate 250 mg γ-alumina with 197 μl of a solution containing 0.006 moles/liter of copper nitrate hemipentahydrate and 0.006-mol/l of gallium nitrate hydrate dissolved in $H_2O$. The amount of Cu in the total doped weight of the γ-alumina substrate is 300 ppm and the amount of Ga is 300 ppm.

Ex 4: Replicate Ex 1 but impregnate 500 mg γ-alumina with 404 μl of a solution containing 0.006 mol/l of copper nitrate hemipentahydrate and 0.054 mol/l of lithium nitrate dissolved in $H_2O$. The amount of Cu in the total doped weight of the γ-alumina substrate is 300 ppm and the amount of Li is 300 ppm.

Ex 5: Replicate Ex 2 but impregnate 250 mg γ-alumina with 197 μl of a solution containing 0.006 mol/l of copper nitrate hemipentahydrate and 0.016 mol/l of magnesium nitrate hexahydrate dissolved in $H_2O$. The amount of Cu in the total doped weight of the γ-alumina substrate is 300 ppm and the amount of Mg is 300 ppm.

Ex 6: Replicate Ex 2 but impregnate 250 mg γ-alumina with 197 μl of a solution containing 0.007 moles/liter of tin chloride, 7.8 μl of hydrochloric acid, and 0.07 mol/l of lithium nitrate dissolved in $H_2O$. The amount of Sn in the total doped weight of the γ-alumina substrate is 600 ppm and the amount of Li is 400 ppm.

Ex 7: Replicate Ex 2 but impregnate 250 mg γ-alumina with 197 μl of a solution containing 0.002 mol/l of bismuth nitrate pentahydrate and 0.003 mol/l of cesium nitrate dissolved in $H_2O$. The amount of Bi in the total doped weight of the γ-alumina substrate is 300 ppm and the amount of Cs is 300 ppm.

Ex 8: Replicate Ex 2 but impregnate 250 mg γ-alumina with 197 μl of a solution containing 0.012 mol/l of diammonium hydrogenphosphate and 0.016 mol/l of magnesium nitrate hexahydrate dissolved in $H_2O$. The amount of P in the total doped weight of the γ-alumina substrate is 300 ppm and the amount of Mg is 300 ppm.

Comp 1 shows that use of the undoped γ-alumina substrate at 290° C. results in a $[1-octene]_{pur}$ mol % value of 93.6. Comp 2 shows that use of the undoped γ-alumina substrate at 260° C. results in an increased $[1-octene]_{pur}$ value of 96.8.

However, use of the undoped γ-alumina substrate at 260° C. in Comp 2 results in a markedly lower [MOE]$_{conv}$, e.g., 62.8 as compared to 97.9 in Comp 1, and a markedly lower [1-octene]$_{yld}$, e.g., 56.4 as compared to 90.7 in Comp 1.

Ex 1 shows doping the γ-alumina substrate with 600 ppm Cu increases the [MOE]$_{conv}$ to 86.6, as contrasted to 62.8 in Comp 2, while the [1-octene]$_{sel}$ increases to 92.1, as contrasted to 89.9 in Comp 2, and the [1-octene]$_{yld}$ increases to 79.7, as contrasted to 56.4 in Comp 2. These improved results are obtained while maintaining the [1-octene]$_{pur}$ at or above a minimum of 96.0, e.g., 96.1, when the reaction is performed at 290° C., as contrasted to the [1-octene]$_{pur}$ value of 93.6 shown in Comp 1.

Ex 2 shows that doping with a combination of 600 ppm Cu and 400 ppm Zn, increases [MOE]$_{conv}$ to 81.8, [1-octene]$_{sel}$ to 94.4, and [1-octene]$_{yld}$ to 77.2 values, as contrasted to Comp 2. Notably, the [1-octene]$_{sel}$ mol % of 94.4 is increased above that shown in Ex 1.

Ex 5 shows that doping with a Cu 300/Mg 300 combination also increases the [MOE]$_{conv}$ to 85.4, the [1-octene]$_{sel}$ to 92.0, and the [1-octene]$_{yld}$ to 78.6 values, as contrasted to Comp 2.

Exs 3 and 4 show that reducing the concentration of Cu to 300 ppm when doping in combinations with 300 ppm Ga (Ex 3) or 300 ppm Li (Ex 4) lowers values for [MOE]$_{conv}$ and [1-octene]$_{yld}$, as contrasted to mol % values obtained with Ex 1. However, the [1-octene]$_{sel}$ is increased to 93.9 in Ex 3 and increased to 94.1 in Ex 4, as contrasted to 89.9 in Comp 2, and remained close to the value of 94.4 obtained with the Ex 2 combination.

Exs 1, 2, and 5 show that particular dopant elements and combinations of dopant elements increase the [MOE]$_{conv}$ mol % to at least 80.0, as contrasted to 62.8 in Comp 2, while maintaining a [1-octene]$_{pur}$ at or above a minimum of 96.0.

Exs 1, 2, and 5 show that particular dopant elements and combinations of dopant elements increase the [1-octene]$_{yld}$ mol % to at least 75.0, as contrasted to 56.4 in Comp 2. Further, all the Bi, Cs, Ga, Li, Mg, P, Sn, and Zn dopant elements, when used in the combinations shown in the table, and the Cu dopant element, when used alone, increase the [1-octene]$_{sel}$ mol % to above 91.0, as contrasted to 89.9 in Comp 2.

Additionally, particular dopant elements and combinations of dopant elements increase one or more of the [MOE]$_{conv}$, [1-octene]$_{sel}$, and [1-octene]$_{yld}$ mol % values, as contrasted to Comp 2, when the reaction is performed at temp. below 290° C., e.g., at 275-280° C. For instance, Cu 300/Ga 300 (Ex 3) increases the [1-octene]$_{Sel}$ value to 93.9 at 275° C., Sn 600/Li 400 (Ex 6) increases the [1-octene]$_{sel}$ value to 91.9 at 280° C., Bi/Cs 300 300 (Ex 7) increases the [1-octene]$_{sel}$ value to 91.0 at 275° C., and P 300/Mg 300 (Ex 8) increases the [1-octene]$_{sel}$ value to 91.7 at 275° C., as contrasted to 89.9 in Comp 2.

What is claimed is:

1. An improved method for producing alpha-olefin by catalytically cleaving a methyl-octyl ether precursor, comprising using a catalytic composition that includes a gamma-alumina substrate doped with at least one element selected from the group bismuth, copper, gallium, phosphorus, tin, and zinc, an amount of each element being within a range of from 150 parts per million to 1,000 parts per million relative to a total doped weight of the gamma-alumina substrate to catalytically cleave the methyl-octyl ether precursor and increase the yield to alpha-olefin by improving the selectivity to alpha-olefin and/or the conversion of the methyl-octyl ether at a desired alpha-olefin purity relative to an undoped gamma-alumina substrate.

2. The method of claim 1, wherein the alpha-olefin is 1-octene.

3. The method of claim 1, wherein at least one element consists of copper, gallium, tin, zinc or a combination thereof.

4. The method of claim 1, wherein at least one element is copper, zinc or a combination thereof.

5. The method of claim 1, wherein the at least one element is combined with at least one element consisting of cesium, lithium, and magnesium, an amount of each element being within the range of from 150 parts per million to 1,000 parts per million relative to the total doped weight of the gamma-alumina substrate.

* * * * *